United States Patent [19]

Wolf et al.

[11] Patent Number: 5,601,562
[45] Date of Patent: Feb. 11, 1997

[54] FORKED INSERTION TOOL AND METNOD OF ARTHROSCOPIC SURGERY USING THE SAME

[75] Inventors: Eugene M. Wolf, San Francisco, Calif.; Richard D. Grafton, Naples, Fla.

[73] Assignee: Arthrex, Inc., Naples, Fla.

[21] Appl. No.: 388,284

[22] Filed: Feb. 14, 1995

[51] Int. Cl.$^6$ ........................................................ A61F 5/00
[52] U.S. Cl. .............................. 606/86; 128/898; 623/13; 606/72
[58] Field of Search ................................... 606/72, 73, 80, 606/86, 87, 88, 89, 90; 128/898; 623/13

[56] References Cited

U.S. PATENT DOCUMENTS

| | | | |
|---|---|---|---|
| 4,985,032 | 1/1991 | Goble | 606/96 |
| 5,098,435 | 3/1992 | Stednitz et al. | 606/73 |
| 5,266,075 | 11/1993 | Clark et al. | 623/13 |
| 5,350,380 | 9/1994 | Goble et al. | 606/80 |
| 5,354,300 | 10/1994 | Goble et al. | 606/80 |
| 5,393,302 | 2/1995 | Clark et al. | 623/13 |
| 5,397,356 | 3/1995 | Goble et al. | 623/13 |
| 5,423,823 | 6/1995 | Schmiedling | 606/80 |
| 5,431,651 | 8/1995 | Goble | 606/73 |

*Primary Examiner*—Michael Powell Buiz
*Assistant Examiner*—Mark S. Leonardo
*Attorney, Agent, or Firm*—Ostrolenk, Faber, Gerb & Soffen, LLP

[57] ABSTRACT

A double-forked arthroscopic tool is provided for inserting a looped, double strand of semitendinosus tendon into the femoral tunnel during ACL reconstruction. The double strand of tendon is fixed in the tunnel by a transverse implant, which passes just under the apex of the looped tendon, such that the tendon is securely looped over the implant in the femoral tunnel.

4 Claims, 9 Drawing Sheets

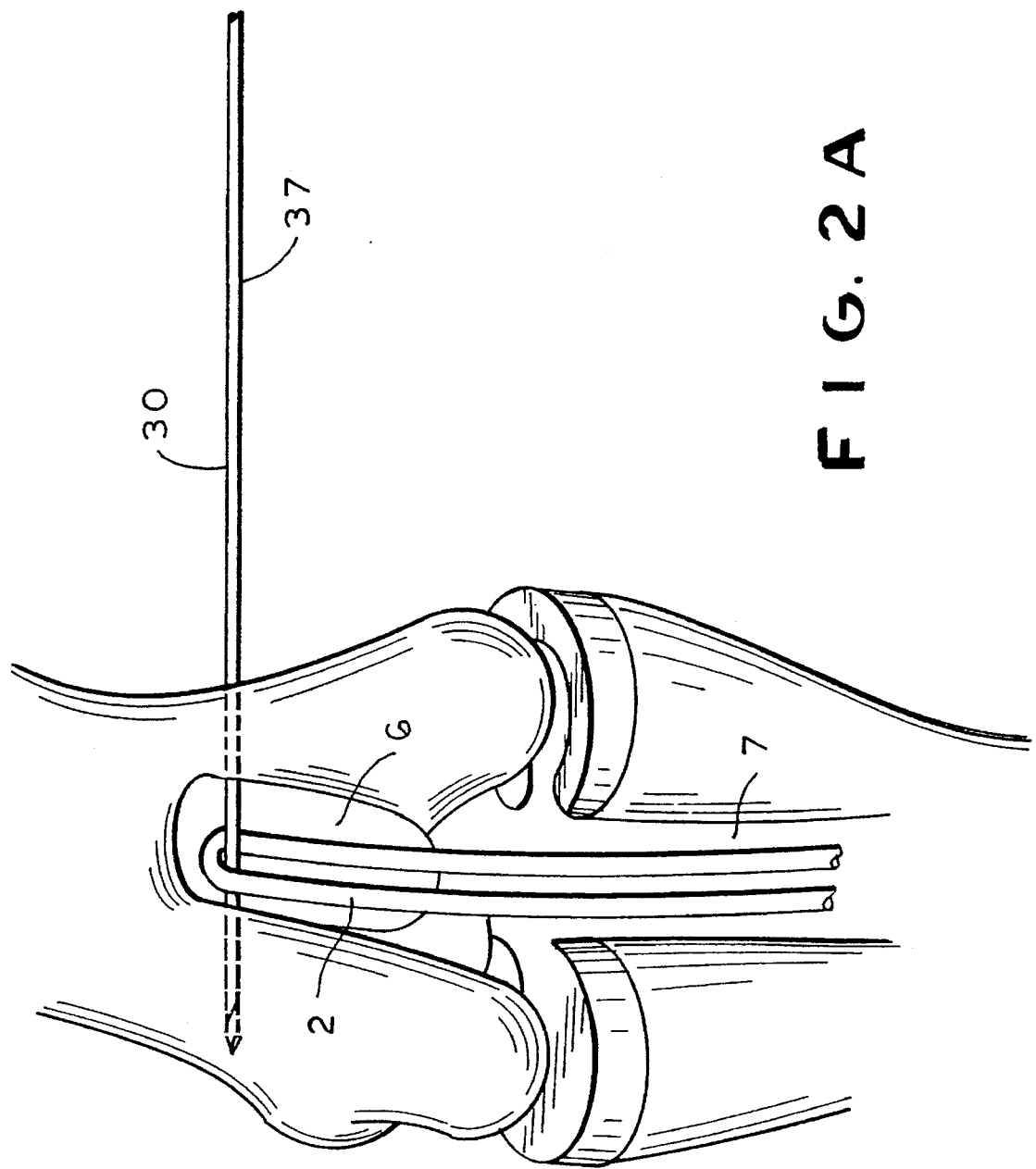

FORKED INSERTION TOOL AND METNOD OF ARTHROSCOPIC SURGERY USING THE SAME

BACKGROUND OF THE INVENTION

1. Field of the Invention

The present invention relates to an arthroscopic instrument for reconstruction of the anterior cruciate ligament (ACL) and to a method of ACL reconstruction using the instrument.

2. Description of the Related Art:

When a ligament or tendon becomes detached from the bone, surgery is usually required to re-secure the ligament or tendon. Often, a substitute ligament or graft is attached to the bone to facilitate re-growth and permanent attachment. Various methods of graft attachment are known, such as staples, suture over buttons, and interference screw fixation.

Staples and suture buttons are disadvantageous because they often do not provide a sufficiently strong attachment to withstand the normal tensile loads to which they are subjected. For example, with suture button fixation, the strand of suture coupling the button and the substitute ligament is the "weakest link in the chain" and if the suture breaks, the ligament will detach.

A stronger graft attachment is obtained by interference screw fixation, in which an interference screw is used to wedge a graft bone block to the wall of a graft tunnel. See, e.g., U.S. Pat. No. 5,211,647, herein incorporated by reference. Although interference screw attachment is more secure than using staples or suture buttons, it is sometimes not possible or desirable to provide such fixation, particularly in the femoral tunnel. For example, in situations where a previous reconstruction has been performed, a new femoral tunnel placed close to the previous tunnel may not allow for interference screw fixation. In other cases, a semitendinosus graft must be used since the previous reconstruction used the mid third patellar tendon. Although a bone-semitendinosus graft-bone construct may be prepared using a workstation as disclosed in allowed U.S. Ser. No. 08/186,604, now U.S. Pat. No. 5,397,357, such a procedure is time consuming, and often undesirable.

Accordingly, a need exists for a fixation technique which provides strong attachment of a semitendinosus graft in the femoral tunnel, without interference screw fixation.

SUMMARY OF THE INVENTION

The present invention fulfills the above-noted need by providing an arthroscopic instrument and method for transverse fixation of the semitendinosus tendon in the femoral tunnel.

In accordance with the present invention, a novel, double-forked marking hook is used to insert a looped, double strand of semitendinosus tendon into the femoral tunnel. The double strand of tendon is fixed in the tunnel by a cylindrical, transverse implant, which passes just under the apex of the looped tendon, such that the tendon is securely looped over the implant in the femoral tunnel.

More generally, the method of the present invention involves the steps of: (a) forming a tunnel in a bone; (b) forming a loop in a graft, the loop lying in a plane and having an apex; (c) inserting the looped graft into the tunnel; (d) guiding a cylindrical implant transversely through the loop of the graft such that the graft is looped over the implant; and (e) securing the graft in the tunnel.

Preferably, the cylindrical implant is cannulated, and the step of guiding the implant transversely through the loop of the graft is performed by: (i) inserting a guide pin through the bone along an axis which is substantially perpendicular to the plane of the loop of the graft and passes through the loop near the apex of the loop, and (ii) advancing the cannulated implant over the guide pin such that it passes through the loop of the graft.

The cylindrical implant is preferably provided in the shape of a shaft with a threaded back end. Preferably, prior to advancing the cannulated implant over the guide pin, a cannulated drill is advanced over the guide pin and rotated to counterbore the bone to receive the threaded back end of the implant. The drill is then removed and a cannulated tunnel shaper, having a diameter smaller than the counterbore, is advanced over the guide pin and tapped into the bone to create a transverse tunnel in the bone for receiving the shaft of the implant.

Next, the cannulated implant is inserted in the transverse tunnel and is secured therein by rotating the implant such that the threaded back end of the implant engages, advances within and becomes fully seated in the counterbore of the tunnel. The guide pin is then removed from the transverse tunnel, leaving the graft looped over the cannulated implant. The graft is then secured in the tunnel through which it was inserted, preferably by wedging the graft against the wall of the tunnel with a bone block.

Preferably, the method of the present invention is used for ACL reconstruction in a blind femoral tunnel, whereby a transtibial tunnel is formed first by removing a bone core from the tibia. The removed bone core is preferably cut in half, and the two bone core halves are appropriately shaped and then used to wedge the graft, looped over the cannulated implant, in the femoral and tibial tunnels, respectively. The loose end of the graft extending from the tibial tunnel is then stapled in place prior to closing the incision.

The present invention is also directed to a forked insertion tool for reconstructive surgery for practicing the above-described method. The forked insertion tool has a double forked tip comprised of a distal pair of prongs forming a distal U-shaped fork for receiving a loop of a graft and a proximal pair of prongs forming a proximal U-shaped fork for receiving a guide pin. The distal U-shaped fork and the proximal U-shaped fork are perpendicular, such that the guide pin is received within the loop of the graft.

The forked insertion tool is adapted to be received in an outrigger formed in the shape of an arc of a circle having a center. A sleeve is coupled to the outrigger. The sleeve has a longitudinal axis extending toward the center of the outrigger circle, and the sleeve is adapted to receive a guide pin.

The forked insertion tool has a proximal end, a distal end, and a central axis extending from the proximal end to the distal end, and is coupled at its proximal end to the outrigger such that the central axis of the insertion tool intersects the longitudinal axis of the sleeve at the center of the circle. The distal end of the tool is provided with a double forked tip for receiving a graft and holding the graft in a loop.

When the forked insertion tool is placed in the outrigger and a graft is laid over the double-forked tip, the apex of the resultant loop in the graft is displaced a predetermined distance from the center of the outrigger circle along the central axis of the forked insertion tool in a direction away from the proximal end of the forked insertion tool.

The predetermined distance described above is preferably approximately equal to the radius of a cannulated cylindrical implant which is slidable over the guide pin.

The outrigger is preferably provided with a longitudinal, arcuate slot, and the forked insertion tool is coupled to the outrigger by an adapter slidably secured in the slot. The adapter is slidable along the outrigger to a plurality of marked positions at which the fork is aligned at various selectable angles formed with respect to the sleeve.

In the preferred embodiment of the invention, the adapter is secured in a position relative to the sleeve such that the central axis of the forked insertion tool and the longitudinal axis of the sleeve are substantially mutually perpendicular.

In summary, the present invention provides a method and apparatus for performing a two-incision, single tunnel arthroscopic graft revision in which the tendon is naturally fixed close to the original insertion point of the original anterior cruciate ligament (ACL). Preferably, the tendon is fixed with a natural, bone-core plug previously removed from the tunnel in the course of forming the tunnel. The inventive method significantly reduces the potential for graft stretching, or "creep." Advantageously, the distance between the natural, over-the-top position to the bone core fixation point is approximately 4.0 mm, compared to the known suture button method discussed above, in which the graft is fixated by suture and painful extra-articular hardware, at distances over 12.0 mm apart.

Additionally, the fixation provided by the present invention avoids graft migration, also known as the "windshield-wiper" effect, which occurs with prior art fixation techniques, such as suture button fixation. The windshield-wiper effect is the lateral movement of a substitute graft from one side of the tunnel to the other during extension and flexion of the knee. As a result of this side-to-side movement, the graft experiences wear and abrasion. In contrast, in the present invention, the graft is secured in the tibial and femoral tunnels with bone plugs, advantageously eliminating the windshield-wiper effect.

Other features and advantages of the present invention will become apparent from the following description of the invention which refers to the accompanying drawings.

BRIEF DESCRIPTION OF THE DRAWINGS

FIG. 2A shows a tendon graft looped over a guide pin within a femoral tunnel, according to a preferred embodiment of the present invention.

DETAILED DESCRIPTION OF THE PREFERRED EMBODIMENT

Figure 1:
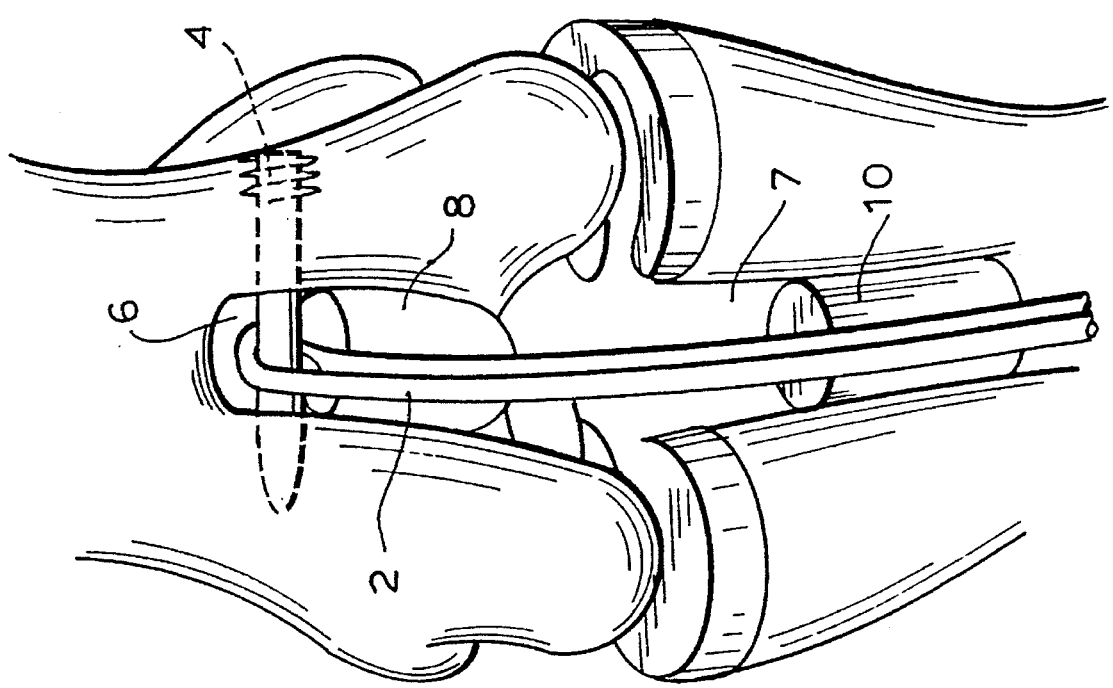
FIG. 1 is a posterior view showing the position of the cylindrical implant of the present invention and a graft tendon looping over the implant in accordance with a preferred method of ACL reconstruction of the present invention.

Referring to FIG. 1, an ACL construct in accordance with a preferred embodiment of the present invention is shown. A graft 2 is shown as looped around a transverse implant 4 in a blind femoral tunnel 6. Graft 2 is wedged in femoral tunnel 6 with a bone plug 8. Graft 2 is wedged in the open-ended tibial tunnel with bone plug 10. As a result of the above-described bone plug fixation, graft 2 does not move laterally in the femoral and tibial tunnels, thereby avoiding the "windshield-wiper" effect described above. In addition, the bone plug fixation in the tunnels is extremely secure, allowing the patient to be ambulatory virtually immediately upon completion of the graft procedure. Strength of the construct improves over time with plug ossification. Further, with placement of graft 2 toward the outer edge of the femoral tunnel, only a small displacement, typically 3–4 mm, exists between the natural, over-the-top position of the ACL and the actual, functional position of graft 2.

Preferably, plugs 8, 10 are formed by removing a bone core from the tibial tunnel during the formation of the tibial tunnel, cutting the bone core in half, and shaping the core halves to form plugs 8, 10. See, e.g., allowed U.S. application Ser. Nos. 08/019,356, now U.S. Pat. No. 5,423,823, and 08/186,604, herein incorporated by reference.

Figure 2:
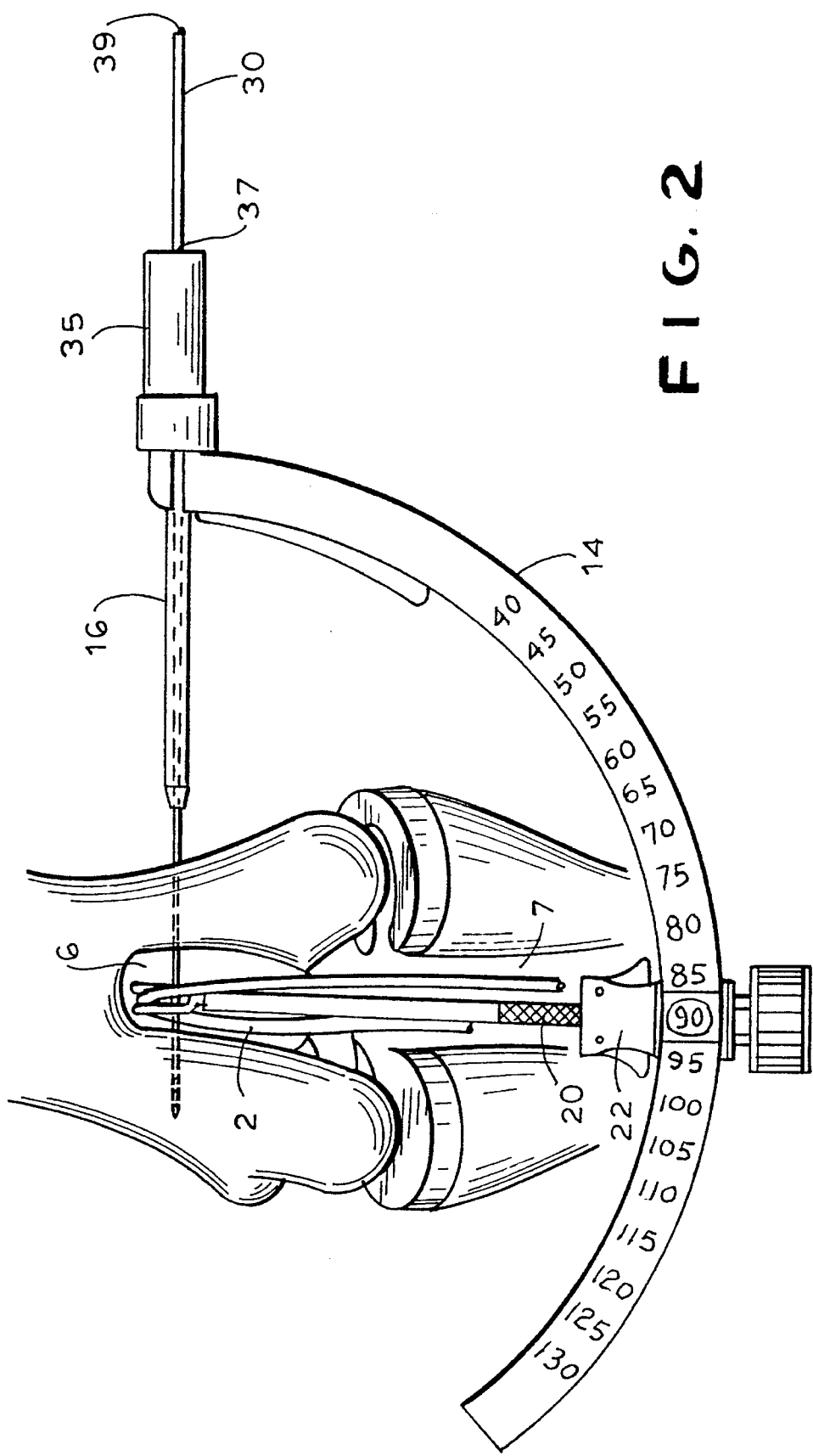
FIG. 2 is a posterior view showing schematically the position of the double-forked insertion hook coupled to the outrigger and the tendon when it is looped over the insertion hook, with the guide pin being inserted using a drill stop in accordance with a preferred method of ACL reconstruction according of the present invention.
Figure 3:
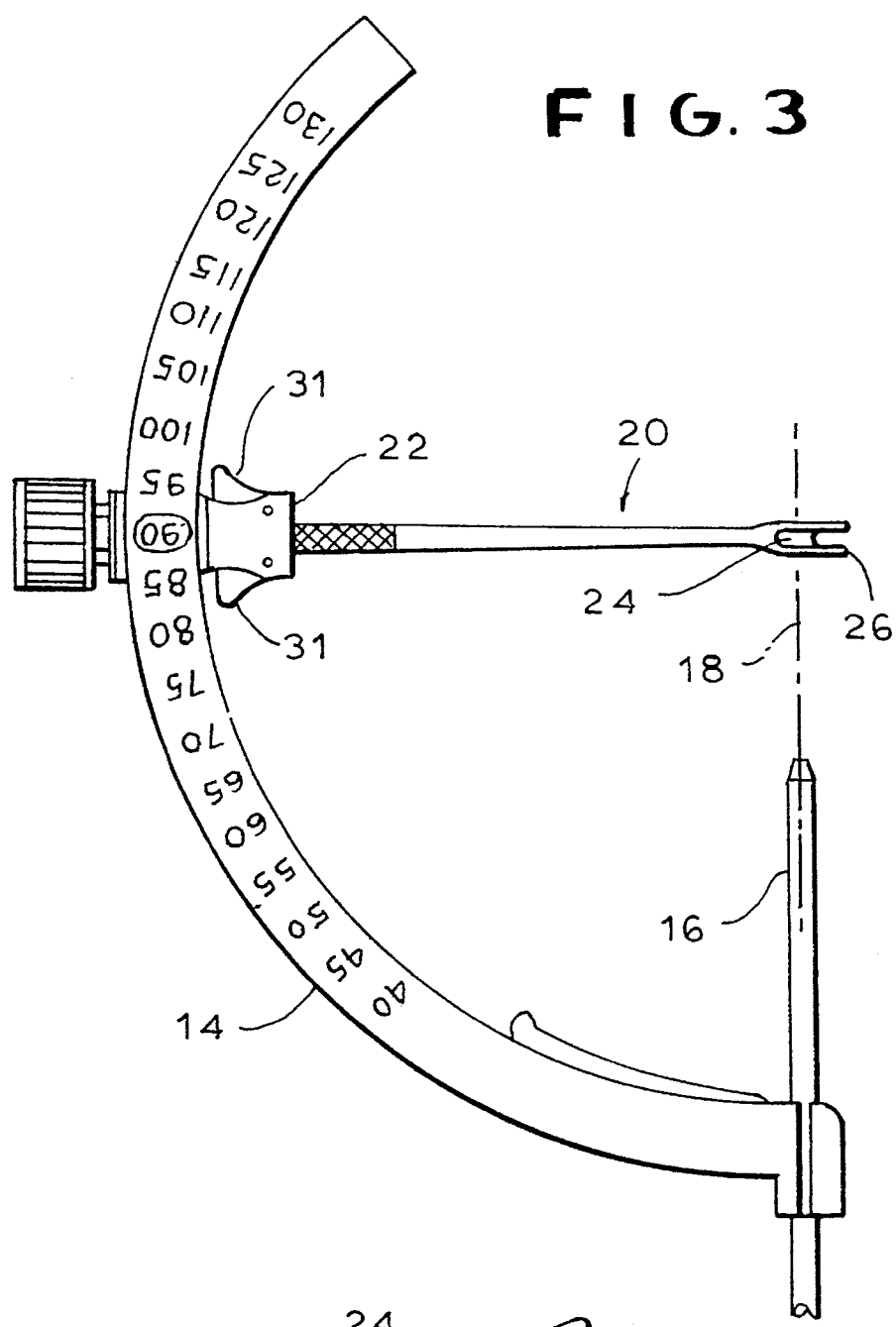
FIG. 3 is a plan view of a preferred apparatus used to perform the preferred ACL reconstruction method according to the present invention.

FIGS. 2 and 3 show a preferred embodiment of the drill guide apparatus for use in conjunction with the present invention. An outrigger 14 having a shape of an arc of a circle has a sleeve 16 coupled to one end such that a central axis 18 of the sleeve intersects the center of the circle. A double-forked insertion tool 20 is attached to outrigger 14 by an adapter 22. Forked insertion tool 20 has a pair of U-shaped forks 24, 26 at its distal end, the more-distal fork 26 being provided to receive a loop of graft 2, as described more fully below.

Adapter 22 is slidably mounted in a slot (not shown) on outrigger 14. Outrigger 14 is preferably marked, typically in degrees, to denote the angular position of forked insertion tool 20 with respect to sleeve 16. A similar type of outrigger is shown in U.S. Pat. No. 5,350,383, the disclosure of which is incorporated herein by reference. In accordance with the present invention, adapter 22 is preferably mounted on outrigger 14 at a position such that the central axis of forked insertion tool 20 is perpendicular to longitudinal axis 18 of sleeve 16.

Figure 4:
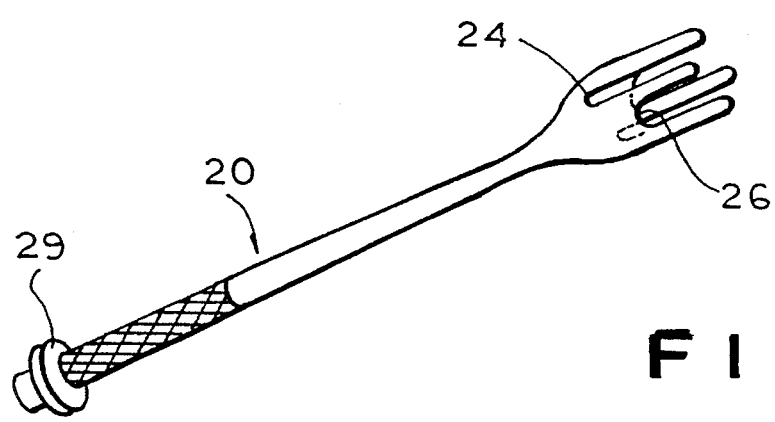
FIG. 4 is a perspective view of the double-forked insertion tool according to a preferred embodiment of the present invention.
Figure 5A:
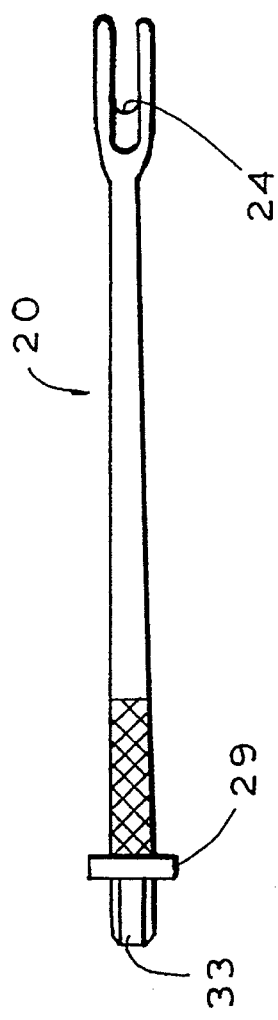
FIGS. 5A and 5B are detail views of the double forked insertion tool of the present invention.
Figure 5B:
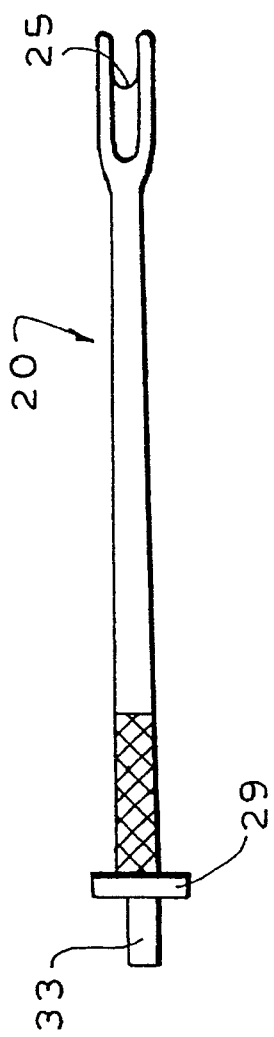

Referring to the perspective view of FIG. 4, and the detailed views of FIGS. 5A and 5B, forked insertion tool 20 is shown according to a preferred embodiment of the invention. As is evident from the drawings, the proximal U-shaped fork 24 is perpendicular to distal U-shaped fork 26. As described in further detail herein, distal fork 26 receives and supports a loop of graft 2, and proximal fork 24 receives a transversely-inserted guide pin 30 for implant 4 and the instruments used to create a transverse tunnel for the implant, as discussed below. Preferably, and for reasons which will become evident from the following discussion, forks 24 and 26 are separated longitudinally by a distance approximately equal to the diameter of the implant 4. The prongs of distal fork 26 are formed of sufficient length to prevent graft 2 from slipping out of the distal fork during insertion of the graft into the femoral tunnel.

At its proximal end, forked insertion tool 20 is provided with a collar 29 which enables the proximal end of the tool to be received in adapter 22 mounted on outrigger 14. Collar 29 is engaged by clasps (not shown) within adapter 22 which are operated by levers 31, shown in FIG. 3. A key 33 is formed by a flat face disposed on the distal end of forked insertion tool 20. Key 33 is received in a flattened hole (not shown) in adapter 22 to hold forked insertion tool 20 in a predetermined radial orientation.

After looped graft 2 has been inserted in blind femoral tunnel 6 using forked insertion tool 20, drill stop 35 is attached as shown. Guide pin 30 is then inserted through sleeve 16 and drilled into the femur in a direction substantially perpendicular to the forked insertion tool 20. See FIG. 2.

Guide pin 30 is provided with a laser-etched, circumferential line 37. Guide pin 30 is drilled into the femur until line 37 reaches the proximal end of drill stop 35. This can be easily accomplished by inserting the guide pin into a chuck of a drill (not shown) up to the position of the line, and then advancing the drill until the drill chuck hits the drill stop 35. Circumferential line 37 is located at a position on guide pin 30 such that guide pin 30 is inserted to a depth where the distal, fluted end of guide pin 30 anchors into cortical bone on the opposite side of the knee joint, with the distal tip of guide pin 30 extending approximately 20 mm beyond forked insertion tool 20.

Due to the perpendicular orientation of forks 25 and 27 of forked insertion tool 20, guide pin 30 passes under distal fork 27 and through the loop of graft 2. After guide pin 30 is in place, drill stop 35, guide sleeve 16, outrigger 14, and forked insertion tool 20 can be removed, at which point the tendon or graft is looped over the guide pin in the femoral tunnel, as shown in FIG. 2A.

Figure 6:
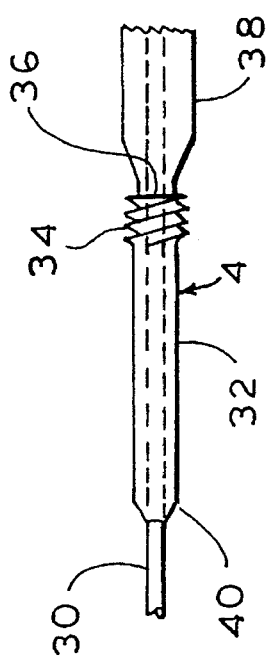
FIG. 6 is a detail of the transverse implant used in the method of the present invention.

Next, a transverse tunnel is created in the femur to accommodate the cannulated implant 4. As shown in FIG. 6, implant 4 has a smooth shank 32, a threaded back end 34, and a socket 36 at the back end for receiving a screwdriver 38, a section of which is shown in FIG. 6. Implant 4 is preferably about 40 mm in length, has a 4.5 mm outer diameter, and has a cannulation sized appropriately to mate with guide pin 30. In the preferred embodiment of the invention, guide pin 30 is a 1.5–2.0 mm K-wire guide pin. Implant 4 is provided with a taper 40 at a distal end thereof, which allows the implant to slide under the tendon or graft which, at this point, is looped over the guide pin.

Figure 7B:
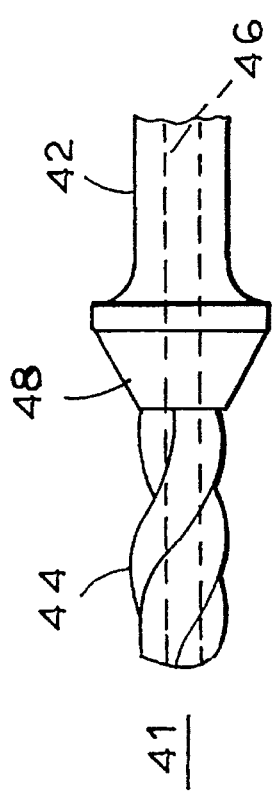
FIGS. 7A and 7B show a cannulated drill used in performing an ACL construct according to a preferred embodiment of the present invention.
Figure 7A:
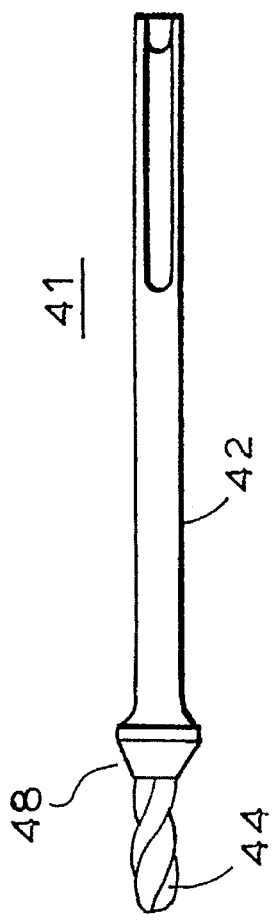
Figure 9:
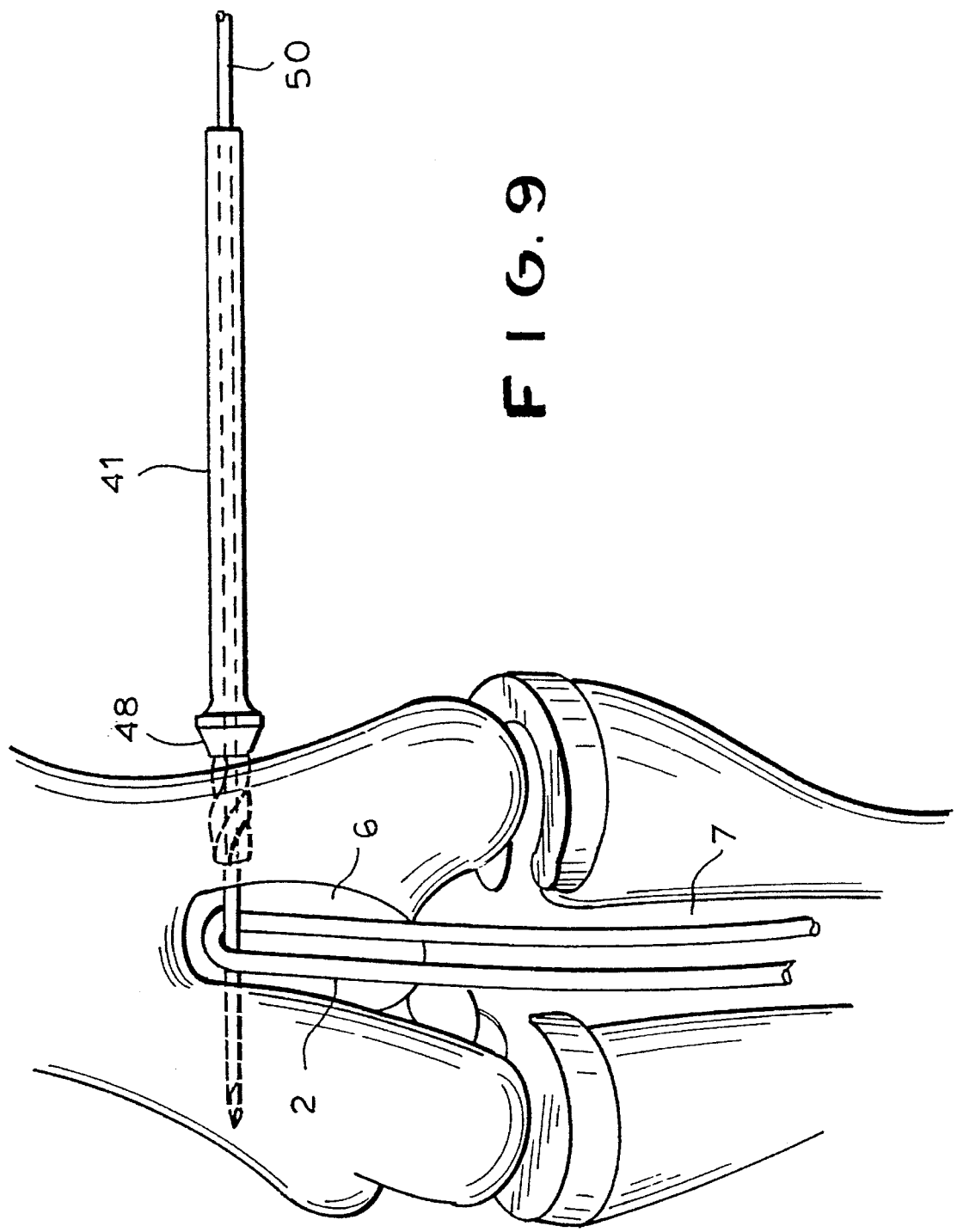
FIG. 9 is a schematic view of the cannulated drill being used to counterbore a femur according to a method of a preferred embodiment of the invention.

To create the transverse tunnel, a cannulated drill 41, shown in FIGS. 7A, 7B, and 9, is first advanced over guide pin 30. Drill 41 has a longitudinal shaft 42, a fluted tip 44, a cannula 46, and a chamfer 48. Using drill 41, cortical bone in the femur is counter-bored to a depth to accommodate the threaded back end 34 of implant 4. Chamfer 48 of drill 41 acts as a depth-stop for the counterbore. Once the counterbore is completed, drill 41 is removed.

Figure 8:
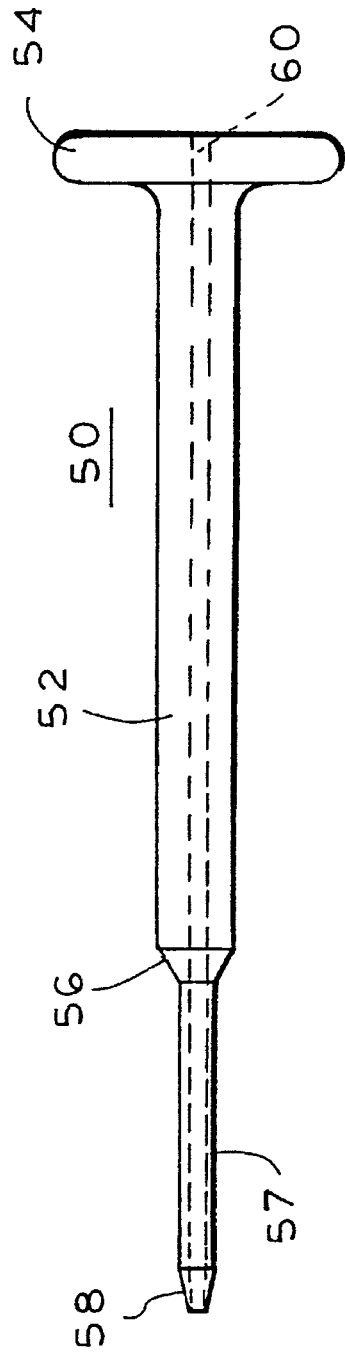
FIG. 8 is a side view of a tunnel shaper used in performing an ACL construct according to a preferred embodiment of the present invention.
Figure 10:
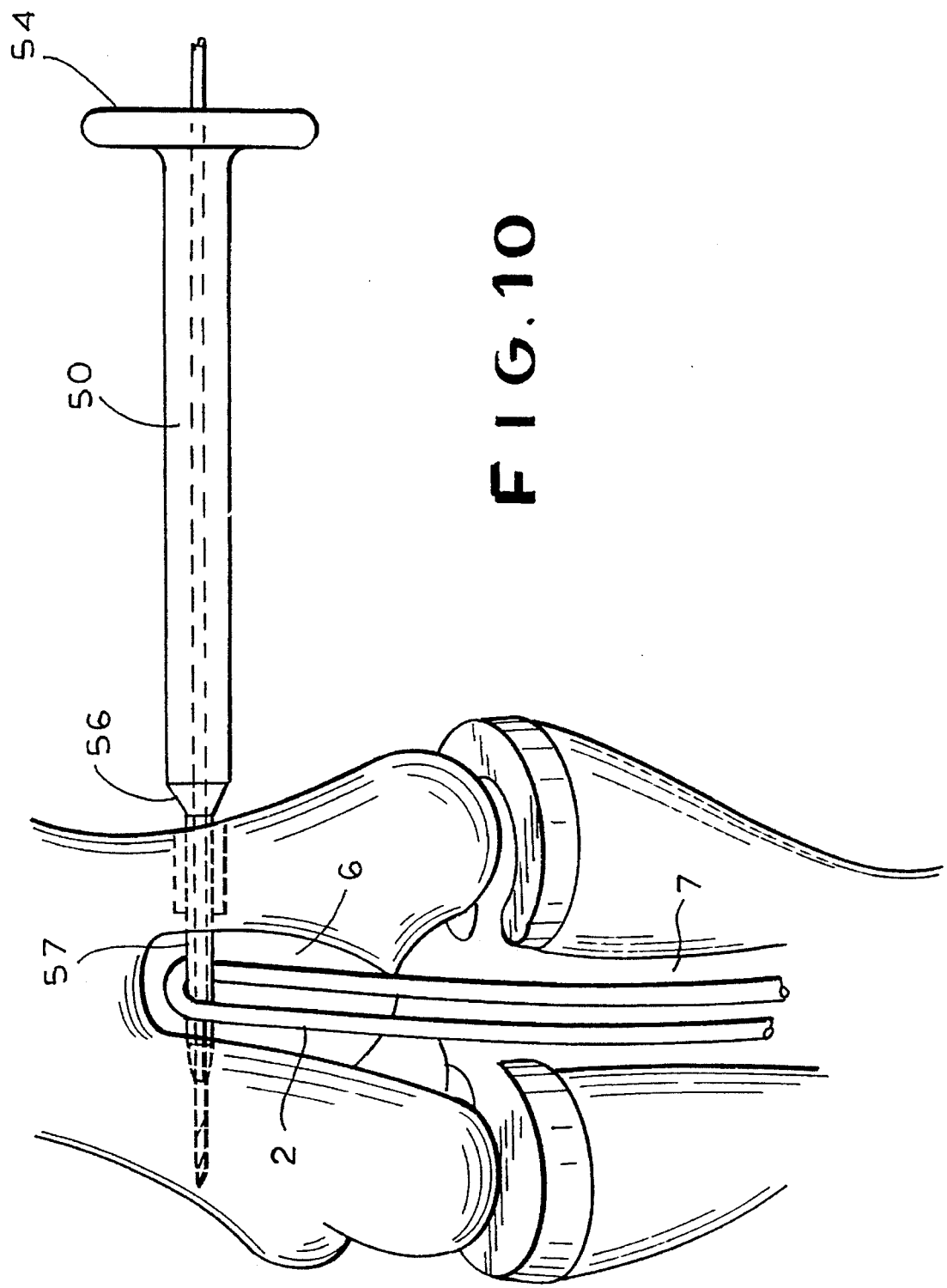
FIG. 10 is a schematic view of the tunnel shaper being used to form a tunnel in a femur according to a method of a preferred embodiment of the invention.

Next, a cannulated tunnel shaper 50, shown in FIGS. 8 and 10, is advanced over the guide pin and tapped into the bone, thus forming a transverse tunnel in the cancellous bone for receiving longitudinal shank 32 of implant 4. Tunnel shaper 50 is tapped into the knee, rather than drilled, to avoid any rotation which might wrap the looped graft around the tunnel shaper shaft.

Tunnel shaper 50 has a proximal shaft 52 with an impacting head 54 at its back end, a chamfer 56 located approximately at its midpoint, and narrows to a tunnel-forming shaft 57, a distal taper 58, and a cannula 60 which extends the length of the shaper. Tunnel shaper 50 is slid over the guide pin into the counterbore, and tapped into the femur until chamfer 56 abuts against the open end of the counterbore. Chamfer 56 can partially enter the counterbore, and acts as a depth-stop for tunnel shaper 50. At this point, the transverse-implant tunnel is completely formed, and the cannulated tunnel shaper 50 is retracted and removed.

Figure 11:
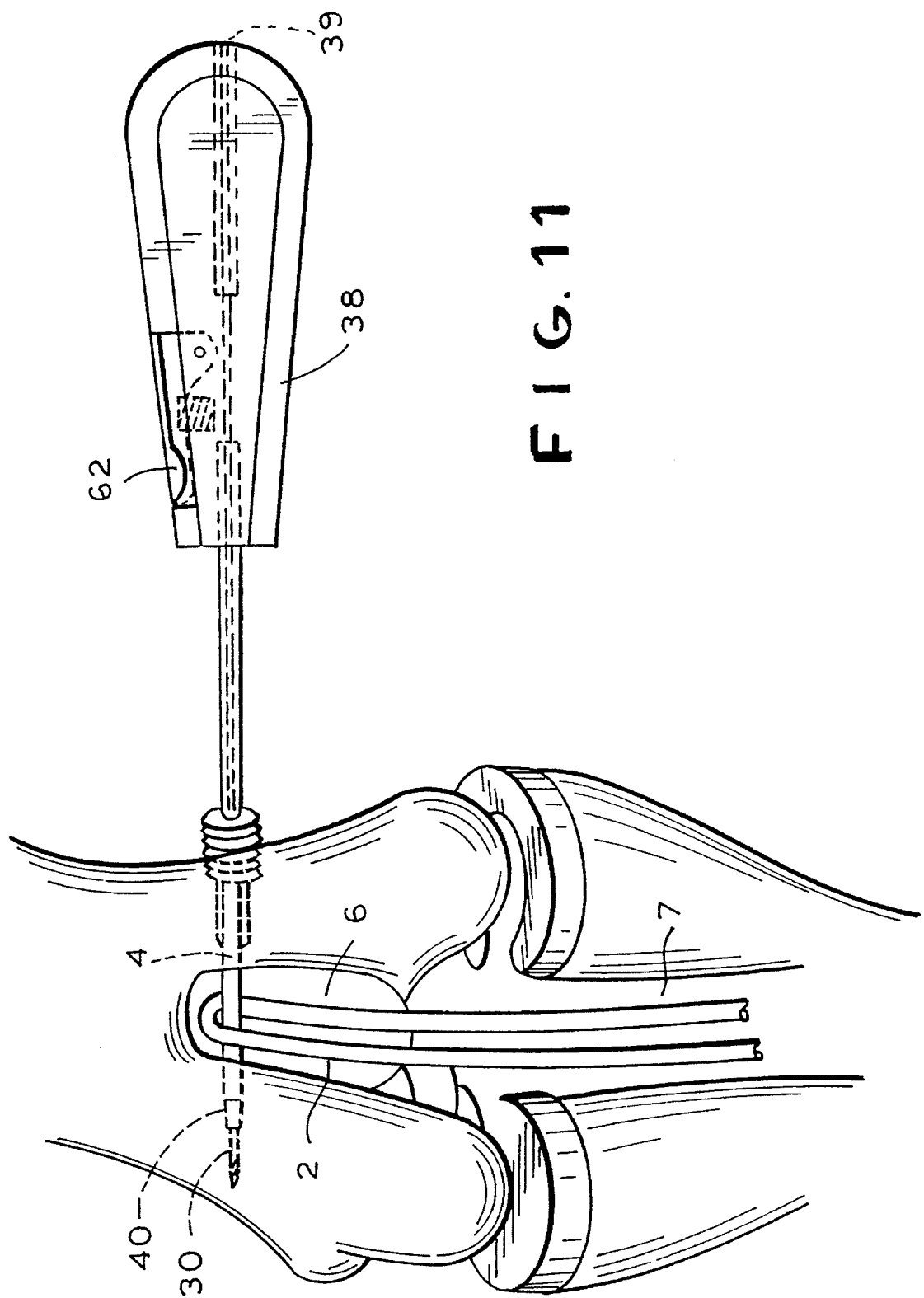
FIG. 11 is a schematic view of a cannulated screwdriver being used to secure an insert in a lateral tunnel in a femur according to a method of a preferred embodiment of the invention.

Next, referring to FIG. 11, cannulated cylindrical implant 4 is placed over guide pin 30 and advanced over the guide pin through the transverse tunnel until taper 40 of implant 4 slips under looped graft 2. The implant is advanced further through the transverse tunnel and screwed into the bone using cannulated screwdriver 38, which is provided with a tip which mates with socket 36 of the implant. When implant 4 is fully seated in the transverse tunnel, graft 2 is looped over the implant at approximately the lateral midpoint of the smooth shank 32 of the implant.

The end 39 of pin 30, when flush with the proximal end of screwdriver 38, acts as the depth control for the screw. The end 39 of the pin aligns with the proximal end of the handle of cannulated screwdriver 38 when implant 4 is advanced to a position such that implant shank 32 is centered, approximately, with respect to femoral tunnel 6.

With the implant fully inserted in the transverse tunnel, guide pin 30 is removed using the driver 41 and locking device 62, and femoral bone plug 8, having been shaped as discussed above, is inserted into femoral tunnel 3 to secure graft 2 in place. Preferably, the loop of graft 2 is wedged along an upper side of femoral tunnel 6 by bone plug 8 as shown in FIG. 1, such that the graft is positioned as close as possible to its natural, over-the-top location on the upper side of the femur. The free end of graft 2 is wedged in the tibial tunnel 7 using bone plug 10. The loose ends of graft 2 extending from tibial tunnel 7 are then stapled against the tibia with a pair of staples prior to closing the incision.

Where ligament reattachment is required at only one site, and a sufficient portion of the ACL remains intact for reattachment, the useable portion of the ACL itself can be used in place of graft 2 as described above. Although the present invention is particularly designed for use with a semitendinosus tendon, graft 2 can also be an allograft, or an artificial tendon.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of arthroscopic surgery using a cannulated, cylindrical implant and a graft, the method comprising the steps of:

(a) forming a tunnel in a bone;

(b) forming a loop in the graft by looping the graft over a distal U-shaped fork of a forked insertion tool, the loop lying in a plane and having an apex;

(c) inserting the looped graft into the tunnel using the forked insertion tool;

(d) inserting a guide pin through the bone along an axis that is substantially perpendicular to the plane of the loop of the graft such that the guide pin extends through a proximal U-shaped fork of the forked insertion tool, the proximal U-shaped fork being perpendicular to the distal U-shaped fork such that the guide pin passes through the inserted graft loop near the apex of the loop;

(e) removing the forked insertion tool, leaving the graft looped over the guide pin;

(f) advancing the cannulated cylindrical implant over the guide pin and into the tunnel, the cannulated cylindrical implant including:
   (i) a smooth cylindrical shank for supporting the looped graft, the smooth cylindrical shank having a first diameter,
   (ii) a back end provided with threads for securing the implant into the bone, the back end having a second diameter greater than the first diameter, and
   (iii) a front end provided with a taper for allowing the implant to slide between the graft and the guide pin;

(g) sliding the implant transversely along the guide pin and between the graft and the guide pin such that the taper slips under the looped graft and the graft is looped over the implant;

(h) coupling a driver to the back end of the implant and rotating the implant with the driver such that the outer threads of the implant screw into the bone; and (i) removing the driver and the guide pin, leaving the implant secured into the bone and extending transversely across the tunnel with the graft looped over the smooth cylindrical shank of the implant.

2. The method of claim 1, further comprising the steps of:

advancing a cannulated tunnel shaper over the inserted guide pin;

tapping the tunnel shaper into the bone for creating a transverse tunnel to receive the smooth cylindrical shank of the implant; and retracting and removing the tunnel shaper prior to the step of advancing the cannulated implant over the guide pin.

3. The method of claim 1, wherein the step of forming the tunnel in the bone includes removing a core from the bone, and wherein the step of securing the looped graft in the tunnel comprises inserting at least a portion of the core back into the tunnel such that the graft is wedged between a wall of the tunnel and the core.

4. The method of claim 3, further comprising the step of shaping the core after removing the core from the bone and before inserting the core back into the tunnel.

* * * * *